United States Patent [19]

Neumann et al.

[11] Patent Number: 4,583,001

[45] Date of Patent: Apr. 15, 1986

[54] SCANNING SYSTEM FOR MAPPING GAS FLOW UNIFORMITY IN A LASER

[75] Inventors: David K. Neumann, Colorado Springs, Colo.; Nicholas R. Pchelkin, Los Lunas, N. Mex.

[73] Assignee: The United States of America as represented by the Secretary of the Air Force, Washington, D.C.

[21] Appl. No.: 475,436

[22] Filed: Mar. 15, 1983

[51] Int. Cl.$^4$ .............................................. G01N 15/07
[52] U.S. Cl. ...................................... 250/573; 250/215
[58] Field of Search ............... 250/573, 574, 342, 215, 250/343, 432 R; 356/339

[56] References Cited

U.S. PATENT DOCUMENTS

| | | | |
|---|---|---|---|
| 3,597,084 | 9/1971 | Pagano | 356/37 |
| 3,663,891 | 5/1972 | Kocher et al. | 331/94.5 |
| 4,229,653 | 10/1980 | Uthe | 250/339 |

*Primary Examiner*—David C. Nelms
*Assistant Examiner*—J. Gatto

*Attorney, Agent, or Firm*—Donald J. Singer; Bobby D. Scearce; John R. Flanagan

[57] ABSTRACT

A scanning system for mapping the degree of uniformity of gas flow in the cavity of a laser includes a carriage mounted for movement along a set of parallel tracks disposed along a side of the laser cavity. The carriage mounts an infrared detector in radiation receiving relationship with the laser cavity. A screw drive mechanism is drivingly coupled to the carriage for moving it in opposite directions on the tracks. Spaced windows along the side of the laser cavity allows passage of radiation from the laser cavity to the detector. Because of the alternating relationship between transmissive windows and non-transmissive plates which defined the windows, successive portions of a voltage signal generated by the detector representing separate measurements can be easily identified with successive positions of the carriage along the laser cavity, and thus with particular successive portions of the laser cavity where each measurement was taken.

6 Claims, 5 Drawing Figures

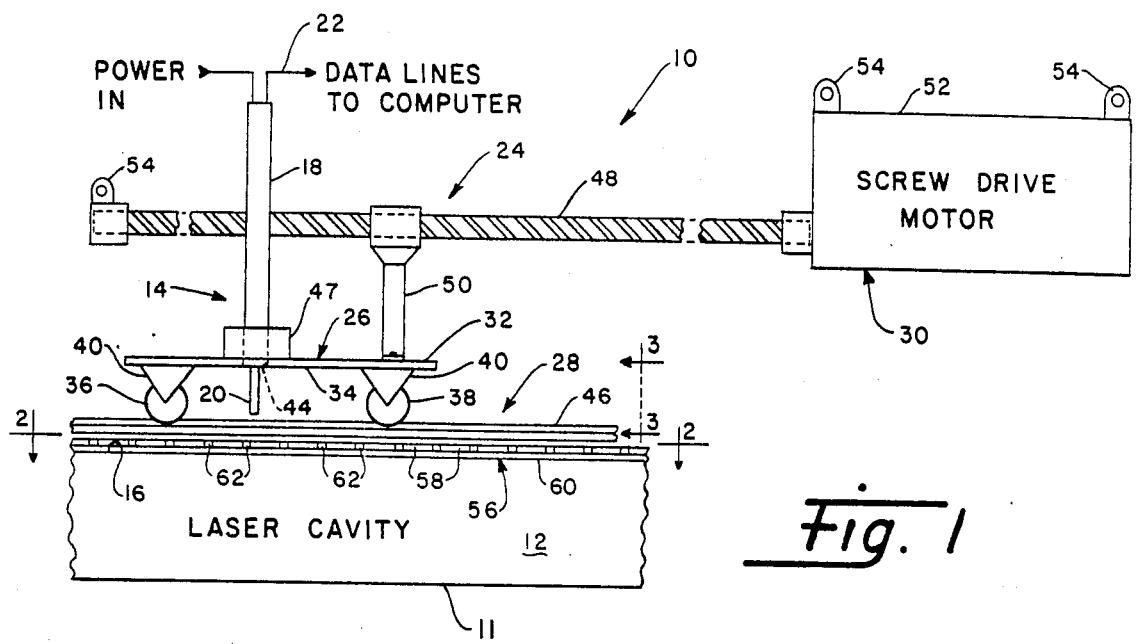

SCANNING SYSTEM FOR MAPPING GAS FLOW UNIFORMITY IN A LASER

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to measurement of operating characteristics of lasers and, more particularly, is concerned with a scanning system for mapping the degree of uniformity of gas flow in the laser cavity.

2. Description of the Prior Art

The short operating duration of a large Air Force $O_2$-I laser, for instance, a period of approximately 30 seconds in length, has made it difficult to achieve a complete understanding of the operating characteristics of the laser. Such understanding is a necessary prerequisite to scaling this laser to higher powers.

Particularly, the spatial concentration profile of $O_2$ molecules and I atoms, as represented by the degree of gas flow uniformity, in the laser cavity is a subject of great concern. Instrumentation presently available is not readily adaptable for use in measuring gas flow in lasers of this type. Consequently, the need exists for a technique for accurately mapping the degree of gas flow uniformity throughout the laser cavity which is relatively easy and inexpensive to carry out.

SUMMARY OF THE INVENTION

The present invention provides a scanning system designed to satisfy the aforementioned needs. The invention integrates commercially available components to provide a low cost scanning system that maps the spatial concentrations of excited diatomic oxygen molecules and iodine atoms in the gas flow of a large $O_2$-I laser. The system can obtain two maps of the gas flow field during the course of a single run cycle. Each map is a graph of a series of electrical voltage output measurements generated by the scanning system which are proportional to the radiation emitted respectively by the $O_2$ molecules and I atoms in the flowing gas in the laser cavity. A series of spaced transmissive windows, defined by spaced non-transmissive plates disposed along the laser cavity, identify the positions where the voltage output measurements were taken along the laser cavity.

Accordingly, the present invention is directed to a scanning system for mapping the degree of gas flow uniformity in a laser cavity, which comprises the combination of: (a) radiation detecting means disposed adjacent a side of the laser cavity in radiation receiving relation thereto for generating a signal proportional to the level of radiation received by the detecting means from the laser cavity, the radiation level being indicative of the concentration of gas flow in the laser cavity; (b) means for moving the detecting means through successive positions along the laser cavity side; and (c) means for identifying portions of the signal which correspond to radiation received at the successive positions of the detecting means along the side of the laser cavity and, thereby, to the concentration of gas flow in the laser cavity adjacent the successive positions therealong.

BRIEF DESCRIPTION OF THE DRAWINGS

FIG. 1 is a fragmentary side elevational view of a scanning system embodying the principles of the present invention.

FIG. 2 is a fragmentary top plan view of a series transmissive windows of the scanning system defined along a side of the laser cavity of FIG. 1 as seen along line 2—2.

FIG. 3 is an enlarged fragmentary end view of a carriage of the scanning system as seen along line 3—3.

DETAILED DESCRIPTION OF THE INVENTION

Figure 5:
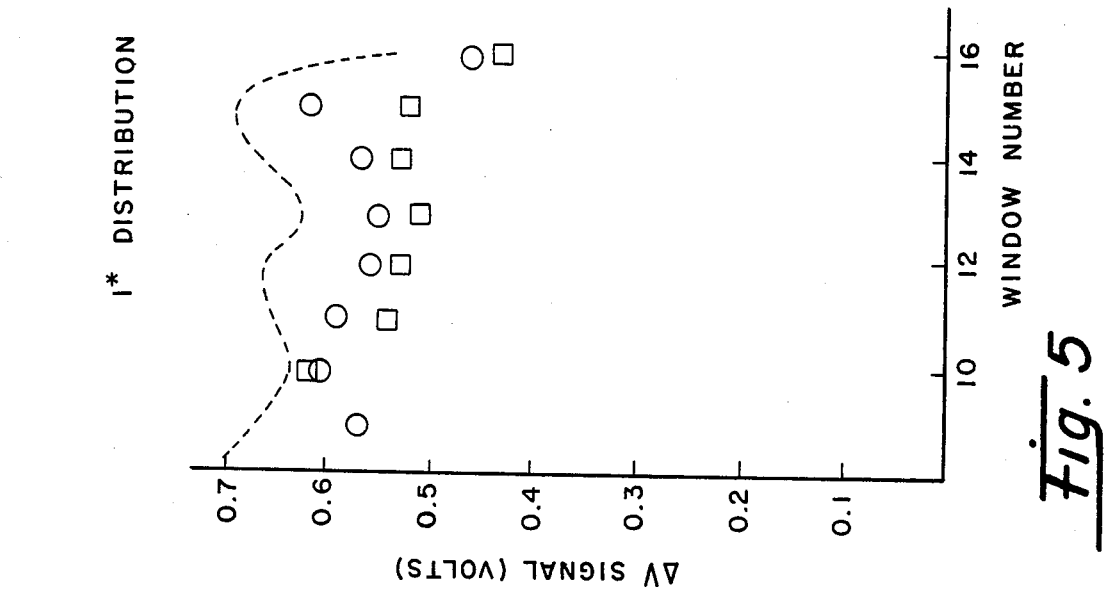
FIGS. 4 and 5 are maps in the form of graphs depicting measurements of the distribution of $O_2$ and I along the laser cavity.

Referring now to the drawings, and more particularly to FIG. 1, there is shown the preferred embodiment of the scanning system of the present invention, being generally designated 10. The scanning system 10 is operable for mapping the degree of uniformity of gas flow along lasing axis 11 in the cavity 12 of a laser.

The scanning system 10 includes radiation detecting means 14 disposed adjacent a side of housing 16 defining the laser cavity 12 in a radiation receiving relationship with respect to the cavity 12. The detecting means 14 is preferably comprised by an infrared liquid nitrogen-cooled intrinsic GE detector 18 which is a component commercially available, and a pinhole collimator 20 which takes the form of an Al tube with a $\frac{1}{2}''$ internal diameter and a $3''$ length. Detector 18 which receives radiation scattered from laser cavity 12 via collimator 20 generates an output signal on data line 22 which is fed to a computer (not shown). The signal is proportional to the level of scattered radiation received by the detector 18 from the laser cavity 12. The scattered radiation level is, in turn, indicative of the concentration of $O_2$ molecules and I atoms in the gas flow along axis 11 in the laser cavity 12.

The scanning system 10 further includes means, generally designates 24 for moving the detecting means 14 through successive positions along the side of housing 16 parallel to axis 11 of laser cavity 12. The moving means 24 includes mounting means 26, guiding means 28 and driving means 30.

The mounting means 26 preferably takes the form of a carriage 32 comprised by a flat platform 34 supported by front and rear pairs of casters 36, 38 attached to the underside of the platform by brackets 40. Each of the casters 36, 38 has a central circumferential groove 42 (FIG. 3) formed therein.

The detector 18 and collimator 20 are mounted at a central location on the platform by any suitable means. For instance, the collimator 20 may be attached to the lower end of the detector 18 which extends through a suitable opening 44 in the platform 34, with the detector, in turn, mounted in its vertical orientation of FIG. 1 by a concentric sleeve 47 fixed to the upper side of the platform and into the central bore of which the detector 18 is threadably secured.

For moving the carriage 32 along the side of housing 16 defining of the laser cavity 12, a linear path of movement is defined by the guiding means 28, preferably in the form of a pair of $\frac{3}{4}''$ angle tracks 46, and a motive force for moving the carriage 32 along the tracks 46 is provided by the driving means 30. As seen in FIG. 3, the tracks 46 are aligned parallel to one another along the side 16 of the laser cavity 12 and are adapted to be received in the respective grooves 42 of the casters 36, 38. The driving means 30 includes an elongated screw 48 which is drivingly coupled to bracket 50 which, in turn, is rigidly attached to the upper side of the platform 34. Also, a drive motor 52 is operatively connected to the screw for rotatably driving the same. Rotation of the screw 48 in a given direction thus causes movement of the carriage 32 along the linear path defined by tracks 46. Reverse rotation of the screw moves the carriage 32 in the opposite direction. The outer end of the screw 48 and the opposite ends of the motor are supported by brackets 54 in the desired position above the laser cavity 12 and carriage 32. The screw and drive motor are components adapted from a conventional garage door opener.

Finally, the scannning system 10 includes means, generally designated 56, for identifying portions of the signal generated by the detector 18 with successive positions of the detector along the side of housing 16 defining laser cavity 12 where radiation generating the signal was received by the detector. In such manner, the concentration of gas flow in the laser cavity and the corresponding portions of the cavity where the successive measurements were taken may be readily determined. Means 56 preferably takes the form of a series of non-transmissive strips or plates 58 mounted in equally spaced apart relationship along a pair of support rails 60. Radiation transmissive windows 62 are defined between the plates 58.

Figure 4:
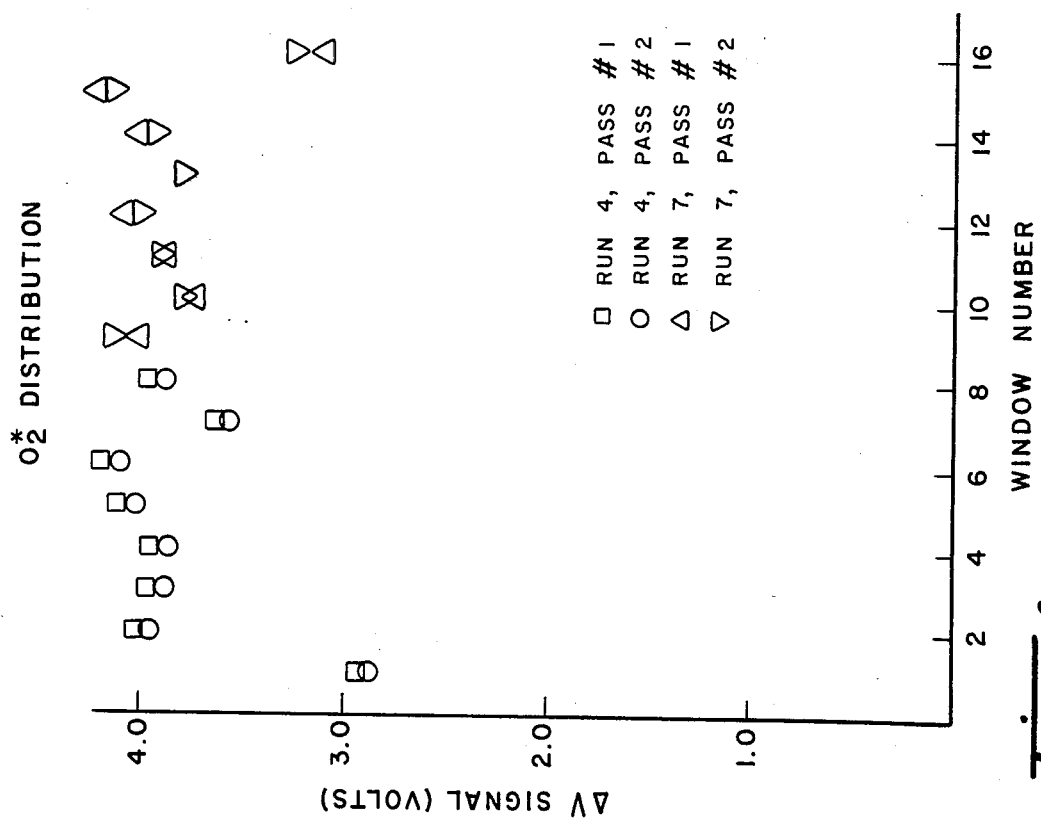

Data taken from the scanning system and recorded on a computer is shown in FIGS. 4 and 5. The data in FIG. 4 shows the average of ten sample points taken at each transmissive window. The data is a composite of several tests where the excited oxygen emission was observed. The labels on the horizontal axis referred to the window position numbers. FIG. 5 shows the same type of data for excited iodine atom emission where only one-half of the laser cavity has been mapped (windows 9 through 16).

It is thought that the improved scanning system of the present invention and many of its attendant advantages will be understood from the foregoing description and it will be apparent that various changes may be made in the form, construction and arrangement of the parts thereof without departing from the spirit and scope of the invention or sacrificing all of its material advantages the form hereinbefore described being merely a preferred or exemplary embodiment thereof.

Having thus described the invention, what is claimed is:

1. A scanning system for mapping the degree of uniformity of radiation emitting gaseous constituents in a gas flow within the cavity of a laser, comprising:
   (a) radiation detection means disposed adjacent said laser cavity in radiation receiving relationship thereto for generating a signal proportional to the level of radiation received by said detection means from said laser cavity, said radiation level being indicative of the concentration of a corresponding one of said radiation emitting gaseous constituents of said gas flow in said laser cavity;
   (b) means for moving said detection means along substantially the length of said laser cavity; and
   (c) means for identifying portions of said signal which correspond to said radiation received at each of a plurality of positions of said detection means along the length of said laser cavity, said signal portions corresponding to the concentration of said radiation emitting gaseous constituents of said gas flow in said laser cavity near corresponding said positions.

2. The scanning system as recited in claim 1, wherein said detection means includes:
   an infrared detector; and
   a pinhole collimator disposed between said detector and said laser cavity.

3. The scanning system as recited in claim 1, wherein said moving means includes:
   means for mounting said detection means for movement along substantially the length of said laser cavity;
   means for guiding said mounting means in a linear path of movement; and
   means for driving said mounting means and said detection means therewith in said linear path of movement along substantially the length of said laser cavity.

4. The scanning system as recited in claim 3, wherein:
   said mounting means includes a platform having first and second ends for mounting said detection means in said radiation receiving relationship to said laser cavity, said platform including a pair of casters at each said end for supporting said platform, each caster having a circumferential groove formed therein;
   said guiding means includes a pair of tracks aligned parallel to one another along substantially the length of said laser cavity, said tracks adapted to be received in said respective grooves of said casters; and
   said driving means includes an elongated screw drivingly coupled to said platform and a drive motor operatively connected to said screw for rotatably driving the same.

5. The scanning system as recited in claim 1, wherein said identifying means includes a series of strips disposed in spaced apart relationship along substantially the length of said laser cavity to define a series of windows therebetween through which said radiation emitted by said radiation emitted gaseous constituents from said laser cavity may be received by said detection means.

6. A scanning system for mapping the degree of uniformity of radiation emitting gaseous constituents in a gas flow within the cavity of a laser, comprising:
   (a) a platform disposed adjacent said laser cavity for movement along substantially the length of said cavity;
   (b) a pair of rotatable casters supporting said platform at each end thereof, each caster having a circumferential groove formed therein;
   (c) an infrared detector mounted on said platform in spaced, radiation receiving relationship relative to said laser cavity, said detector generating a signal proportional to the level of radiation received by said detector from said laser cavity, said radiation level being indicative of the concentration of said radiation emitting gaseous constituents of said gas flow in said laser cavity;
   (d) a pinhole collimator mounted to said platform between said detector and said laser cavity;
   (e) a pair of tracks aligned parallel to one another along substantially the length of said laser cavity and adapted to be received in said respective grooves of said casters, said tracks defining a linear path of movement along said cavity for said platform and said detector and collimator mounted thereto;

(f) an elongated screw drivingly coupled to said platform;

(g) a drive motor operatively connected to said screw for rotatably driving the same and causing movement of said platform along substantially the length of said laser cavity; and (h) a series of strips disposed in spaced apart relationship along substantially the length of said laser cavity and defining a series of windows therebetween through which radiation from said laser cavity may be received by said detector via said collimator, said windows identifying portions of said signal which correspond to radiation received at a plurality of positions of said detector along the length of said laser cavity which signal portions correspond to the concentration of said radiation emitting gaseous constituents of said gas flow in said laser cavity near corresponding said positions.

* * * * *